United States Patent
Rooney et al.

(10) Patent No.: US 7,470,239 B1
(45) Date of Patent: Dec. 30, 2008

(54) HIGH PERFORMANCE COIL WIRE

(75) Inventors: Maura Rooney, Cambridge, MA (US);
Joseph Richard, Bedford, MA (US);
Andy Kapravy, Stoughton, MA (US);
Clifford M. Liu, Randolph, MA (US);
Michael S. H. Chu, Brookline, MA
(US); Tom Mirarchi, Shrewsbury, MA
(US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/597,179

(22) Filed: Jun. 20, 2000

Related U.S. Application Data

(63) Continuation of application No. 09/078,946, filed on May 14, 1998, now Pat. No. 6,306,105.

(51) Int. Cl.
*A61B 5/00* (2006.01)
*A61M 25/00* (2006.01)

(52) U.S. Cl. ...................................... 600/585
(58) Field of Classification Search ................ 600/585, 600/433, 434
See application file for complete search history.

(56) References Cited

U.S. PATENT DOCUMENTS

| | | | |
|---|---|---|---|
| 4,080,706 A | 3/1978 | Heilman et al. | 29/173 |
| 4,534,363 A | 8/1985 | Gold | 128/772 |
| 4,545,390 A | 10/1985 | Leary | 128/772 |
| 4,619,274 A | 10/1986 | Morrison | |
| 4,676,249 A | 6/1987 | Arenas et al. | 128/657 |
| 4,721,117 A * | 1/1988 | Mar et al. | 600/585 |
| 4,748,986 A * | 6/1988 | Morrison et al. | 600/585 |
| 4,763,647 A * | 8/1988 | Gambale | 600/585 |
| 4,832,047 A * | 5/1989 | Sepetka et al. | 600/585 |
| 4,841,976 A | 6/1989 | Packard et al. | 128/657 |
| 4,925,445 A | 5/1990 | Sakamoto et al. | 604/95 |
| 4,932,419 A | 6/1990 | de Toledo | 128/772 |
| 4,984,581 A | 1/1991 | Stice | 128/772 |
| 4,991,602 A | 2/1991 | Amplatz et al. | 128/772 |
| 5,052,404 A * | 10/1991 | Hodgson | 600/585 |
| 5,067,489 A | 11/1991 | Lind | 128/772 |
| 5,069,226 A | 12/1991 | Yamauchi et al. | 128/772 |
| 5,118,907 A * | 6/1992 | Stout et al. | 174/135 |
| 5,120,308 A | 6/1992 | Hess | 604/95 |
| 5,129,890 A | 7/1992 | Bates et al. | 604/281 |
| 5,143,122 A * | 9/1992 | Adkins | 138/109 |
| 5,147,317 A | 9/1992 | Shank et al. | 604/164 |
| 5,154,705 A * | 10/1992 | Fleischhacker et al. | 604/526 |
| 5,171,383 A | 12/1992 | Sagaye et al. | 148/564 |
| 5,174,302 A * | 12/1992 | Palmer | 600/585 |
| 5,213,111 A | 5/1993 | Cook et al. | 128/772 |
| 5,228,453 A | 7/1993 | Sepetka | 128/772 |

(Continued)

FOREIGN PATENT DOCUMENTS

CA  2 209 637  7/1996

(Continued)

*Primary Examiner*—Max Hindenburg
*Assistant Examiner*—Jonathan M Foreman
(74) *Attorney, Agent, or Firm*—Finnegan, Henderson, Farabow, Garrett and Dunner LLP

(57) ABSTRACT

A high performance coil over-core guide wire. The guide wire incorporates a nickel-titanium core with a stainless steel coil to provide a wire with improved kink resistance and good pushability.

54 Claims, 2 Drawing Sheets

U.S. PATENT DOCUMENTS

| | | | | |
|---|---|---|---|---|
| 5,230,348 A | | 7/1993 | Ishibe et al. | 128/772 |
| 5,238,004 A | | 8/1993 | Sahatjian et al. | 128/772 |
| 5,242,759 A | | 9/1993 | Hall | 428/610 |
| 5,243,996 A | | 9/1993 | Hall | 128/772 |
| 5,259,393 A | | 11/1993 | Corso, Jr. et al. | 128/772 |
| 5,282,478 A | | 2/1994 | Fleischhaker, Jr. et al. | 128/772 |
| 5,303,714 A | | 4/1994 | Abele et al. | 128/772 |
| 5,333,620 A | | 8/1994 | Moutafis et al. | 128/772 |
| 5,354,257 A | * | 10/1994 | Roubin et al. | 600/7 |
| 5,354,623 A | | 10/1994 | Hall | 428/610 |
| 5,363,847 A | | 11/1994 | Viera | 128/657 |
| 5,365,942 A | | 11/1994 | Shank | 128/772 |
| 5,368,048 A | | 11/1994 | Stoy et al. | 128/772 |
| 5,368,049 A | | 11/1994 | Raman et al. | 128/772 |
| 5,372,144 A | | 12/1994 | Mortier et al. | 128/772 |
| 5,373,856 A | * | 12/1994 | Grenouillet | 600/585 |
| 5,379,779 A | | 1/1995 | Rowland et al. | 128/772 |
| 5,385,152 A | | 1/1995 | Abele et al. | 128/772 |
| 5,415,178 A | * | 5/1995 | Hsi et al. | 600/585 |
| 5,421,349 A | | 6/1995 | Rodriguez et al. | 128/772 |
| 5,443,907 A | * | 8/1995 | Slaikeu et al. | 428/375 |
| 5,458,585 A | * | 10/1995 | Salmon et al. | 600/523 |
| 5,477,864 A | | 12/1995 | Davidson | 128/772 |
| 5,488,959 A | | 2/1996 | Ales | 128/772 |
| 5,498,250 A | | 3/1996 | Prather | 604/280 |
| 5,531,781 A | * | 7/1996 | Alferness et al. | 607/122 |
| 5,542,434 A | | 8/1996 | Imran et al. | 128/772 |
| 5,622,184 A | * | 4/1997 | Ashby et al. | 600/585 |
| 5,636,641 A | | 6/1997 | Fariabi | 128/772 |
| 5,637,089 A | | 6/1997 | Abrams et al. | 604/95 |
| 5,640,970 A | | 6/1997 | Arenas | 128/772 |
| 5,664,580 A | | 9/1997 | Erickson et al. | 128/772 |
| 5,695,111 A | | 12/1997 | Nanis et al. | 228/206 |
| 5,720,300 A | | 2/1998 | Fagan et al. | 128/772 |
| 5,722,424 A | | 3/1998 | Engelson | 128/772 |
| 5,769,796 A | | 6/1998 | Palermo et al. | 600/585 |
| 5,833,631 A | * | 11/1998 | Nguyen | 600/585 |
| 5,840,046 A | | 11/1998 | Deem | 600/585 |
| 5,871,528 A | * | 2/1999 | Camps et al. | 607/122 |
| 5,885,227 A | * | 3/1999 | Finlayson | 600/585 |
| 5,891,055 A | * | 4/1999 | Sauter | 600/585 |
| 5,924,998 A | * | 7/1999 | Cornelius et al. | 600/585 |
| 5,947,940 A | * | 9/1999 | Beisel | 600/525 |
| 5,951,494 A | | 9/1999 | Wang et al. | 600/585 |
| 5,984,878 A | * | 11/1999 | Engelson | 600/585 |
| 5,997,517 A | * | 12/1999 | Whitborne | 604/265 |
| 6,027,460 A | | 2/2000 | Shturman | 600/585 |
| 6,042,876 A | * | 3/2000 | Deem | 427/2.28 |
| 6,106,485 A | * | 8/2000 | McMahon | 600/585 |
| 6,139,540 A | * | 10/2000 | Rost et al. | 600/585 |
| 6,245,030 B1 | * | 6/2001 | DuBois et al. | 600/585 |

FOREIGN PATENT DOCUMENTS

| | | |
|---|---|---|
| CA | 2 251 685 | 9/1998 |
| EP | 0 820 782 A2 | 1/1998 |
| EP | 0 868 924 A2 | 10/1998 |
| JP | 7-7653 U | 2/1995 |
| JP | 08257136 A * | 10/1996 |
| WO | WO 98/39049 | 9/1998 |

* cited by examiner

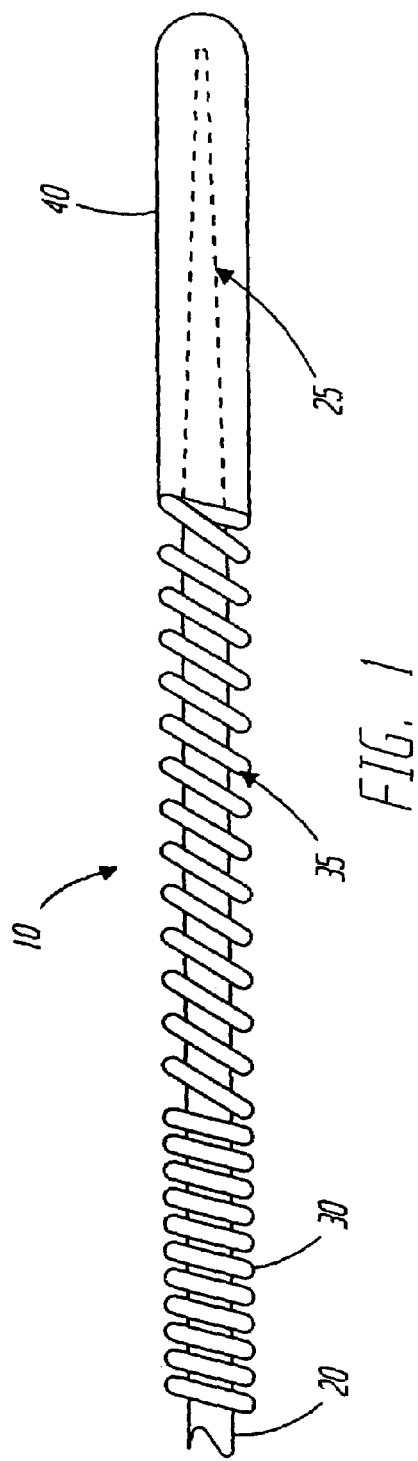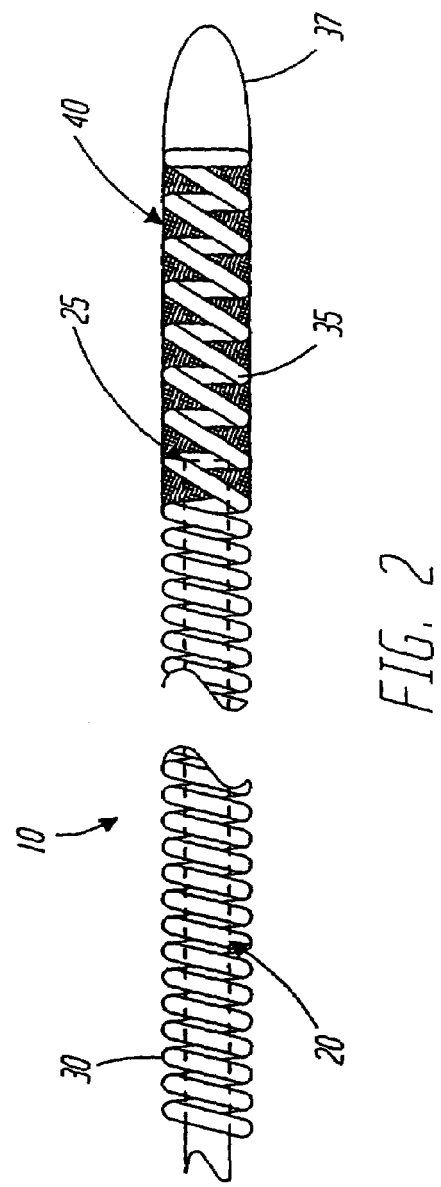

HIGH PERFORMANCE COIL WIRE

This is a continuation of application Ser. No. 09/078,946, filed May 14, 1998 now U.S. Pat. No. 6,306,105.

FIELD OF THE INVENTION

The present invention generally relates to guide wires and their methods of manufacture. Specifically, the present invention relates to guides wires made with a solid core and surrounded by a coil. Those skilled in the art will recognize the benefits of applying the present invention to similar fields not discussed herein.

BACKGROUND OF THE INVENTION

Guide wires are used in a variety of medical applications including intravascular, gastrointestinal, and urological. A common vascular application is Percutaneous Transluminal Coronary Angioplasty (PTCA). This procedure can involve inserting a guide wire through an incision in the femoral artery near the groin, advancing the guide wire over the aortic arch, into a coronary artery, and across a lesion to be treated in the heart. Similarly, angioplasty performed in other parts of the anatomy is called Percutaneous Transluminal Angioplasty (PTA) and may also involve the use of a guide wire. Typical vascular guide wires are 50 cm or 300 cm in length, and are 0.010-0.038 inches in diameter depending upon the application.

Common gastrointestinal uses of guide wires include endoscopic procedures in which an endoscope may be inserted into the mouth and advanced through the esophagus to the bile duct, the cystic duct, or the pancreatic duct. A guide wire is then threaded through a lumen in the endoscope and into the bile duct, cystic duct, or pancreatic duct. Once the distal tip of the guide wire is located in a position desired to be treated, a catheter having a medical instrument on it distal end is advanced over the guide wire and to the treatment area. The guide wire and the catheter may then be observed through the endoscope as treatment occurs.

Urological uses of guide wires include the placement of ureteral stents. Ureteral stenting is required when the normal flow of urine from the kidney into the bladder is compromised perhaps by tumor growth, stricture, or stones. Generally, the procedure involves the insertion of a ureteroscope through the urethra and into the bladder. A guide wire is then advanced through the ureteroscope and into a ureter. The wire is then forced through the compromised portion of the ureter. Once the guide wire is in place, a ureteral stent is advanced over the guide wire and into position in the ureter. The guide wire may then be removed and the stent will maintain the patency of the fluid path between the kidney and the bladder. The procedures described above are but a few of the known uses for guide wires.

Pushability, kink resistance, torqueability and bendability are closely related and important features of a guide wire. It is important that force applied at the proximal end of a guide wire is completely transferred to the distal end of the guide wire. Very stiff wires often provide good pushability (axial rigidity) but poor kink resistance. Kink resistance is measured by the ability of the guide wire to be forced into a relatively tight bend radius without permanently deforming the wire. A guidewire must exhibit good bendability. This characteristic is a balance between adequate flexibility to navigate a tortuous lumen and suitable rigidity to support tracking of another device such as a catheter. Torqueability is closely related to the torsional rigidity of the wire and is ultimately demonstrated by how well rotation imparted to the proximal end of the guide wire is translated to the distal end of the guide wire.

Conventional guide wires are made of carbon steel or stainless steel. More recently, guide wires made of super-elastic alloys have been used. A super-elastic or pseudoelastic metal guide wire was taught in U.S. Pat. No. 4,925,445 to Sakamoto. In U.S. Pat. Nos. 5,238,004 to Sahatjian and 5,230,348 to Ishibe the use of an elastic metal alloy was taught. Sahatjian '004 further teaches that elastic metals may be heat treated to form bends in the wire core and that centerless grinding may be used to create certain wire profiles.

Several different types of guide wires are well known in the art. One type of wire is characterized by a solid metal core surrounded by a metal coil. Typical metals for the core may include spring steels and stainless steels. The distal tip of the core may also be ground to a taper to provide added flexibility near the tip. Coils may be made of the same variety of metals used as core materials. The coil may be made of round wire or flat wire and may surround the entire length of the core or only a portion of the core. The coil usually is formed by helically wrapping the wire around a mandrel, removing the mandrel, and inserting the core into the coil. The pitch of the wire may be varied along the length of the coil to vary the stiffness of the coil.

High performance guide wires usually possess high kink resistance and excellent wire movement. The basic construction of a high performance wire is a Nitinol core surrounded by a lubricious coating. Unfortunately, Nitinol guide wires suffer from diminished pushability because the highly elastic Nitinol absorbs some of the force imparted to the proximal end of the wire. An improved high performance wire would provide better pushability to conventional super-elastic wires.

Traditional coil over core wires provide good axial stiffness and hence improved pushability. Traditional coil over core wires also provide dramatically improved kink resistance over stainless steel wires. However, because the coils tend to wind up on torque, coil over core wires tend to provide reduced torque transmission. Therefore, it would be advantageous to provide a coil over core wire with the torque transmission of a high performance wire.

SUMMARY OF THE INVENTION

The present invention overcomes the deficiencies of the prior art by providing a coil over core guide wire which has the kink resistance and wire movement of a super-elastic wire and the pushability and torque transmission of a coil over core wire. The guide wire has a nickel-titanium alloy core with a tapered distal tip. The core may be super-elastic or linear elastic.

A coil surrounds most of the core and may be bonded to the core. The coil may be stainless steel or nickel-titanium. The coil may be made of flat wire or round wire and may be made of a single strand or multifilar strands and may be a single coil or cross-wound coil.

The guide wire may further have a polymer tip which may be loaded with a radio-opaque material. The wire may also be coated with lubricious coatings. The polymer tip may also form a floppy tip without a safety ribbon.

BRIEF DESCRIPTION OF THE DRAWINGS

FIG. 1 is a cross-section of a first embodiment of the guide wire.

FIG. 2 is a cross-section of a second embodiment of the guide wire.

DETAILED DESCRIPTION OF THE INVENTION

The following detailed description should be read with reference to the drawings in which like elements in different drawing are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

FIG. 1 shows a first embodiment of the guide wire 10. Core 20 may be 50-450 cm in length and 0.008-0.038 inches in diameter depending on the medical application. The distal portion 25 of core 20 may be tapered to provide flexibility to guide wire 10. Preferably the tapered distal portion 25 is formed by grinding 5-20 cm of core 20. The tapered distal portion 25 may be ground into a conical shape with a circular cross-section or stamped such that it has a rectangular cross-section.

Core 20 may be formed of a super-elastic material such as the alloys of nickel and titanium, commonly known as Nitinol. While Nitinol is the most common super-elastic material, any of a variety of other super-elastic materials may be used for core 20. Other alloys by chemical name include; CuAlNi, CuSn, CuZn, InTi, NiAl, FePt, MnCu, and FeMnSi. A detailed discussion of super-elastic alloys and their processing is presented in U.S. Pat. No. 4,925,445 to Sakamoto and is herein incorporated by reference.

In addition to super-elastic materials, linear-elastic materials may be used. Linear-elastic materials are describe in U.S. Pat. No. 5,238,004 to Sahatjian which is also incorporated by reference. In general, linear-elastic materials are composed of the same alloys above. However, different material processing strategies are used to provide a wire which has many of the important characteristics of a super-elastic material without some of the difficulties related to machining, specifically grinding. As such, core 20 may preferably be formed of a linear-elastic alloy of nickel-titanium.

Surrounding core 20 is coil 30. Coil over core wires are well known in the art and are described in detail in U.S. Pat. No. 5,147,317 to Shank which is incorporated by reference. Coil 30 may be made of a variety of metallic materials including super-elastic or linear-elastic materials such as Nitinol, radio-opaque materials such as gold or tungsten, precipitation hardenable alloys such as the non-ferrous cobalt-based alloys MP35N or Elgiloy™ and the ferrous alloys such as K91 from Sanvic Corp. and PH455 from Carpenter, or more conventional stainless steel alloys such as 304. Preferably coil 30 may be 0.001-0.015 inches in diameter, and made of 304 stainless steel.

Figure 4:
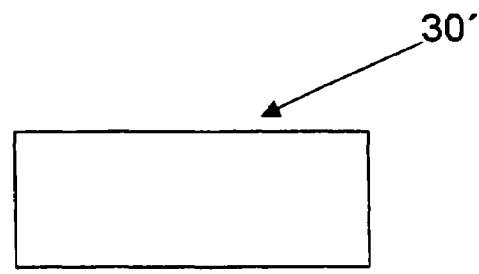
FIG. 4 illustrates a cross-sectional view of a rectangular coil.

Coil 30 is wrapped around substantially the entire length of core 20. Preferably, coil 30 is not wrapped around the tapered distal portion 25 of core 20. Coil 30 may be formed of flat ribbon ranging in dimensions 0.001-0.003 inches in thickness by 0.005 to 0.015 inches in width. FIG. 4 illustrates coil 30' having a rectangular cross-section. Coil 30 is wrapped in a helical fashion about core 20 by conventional winding techniques. The pitch of adjacent turns of coil 30 may be tightly wrapped so that each turn touches the succeeding turn or the pitch may be set such that coil 30 is wrapped about core 20 in an open fashion shown at 35. Preferably, the pitch coil 30 is such that the coils are tightly wrapped over most of the proximal portion of core 20 with the pitch of each turn changing such that coil 30 has an open wrap shown at 35 near the distal end of core 20. Varying the pitch of coil 30 allows guide wire 10 to have a more flexible distal segment.

Figure 3:
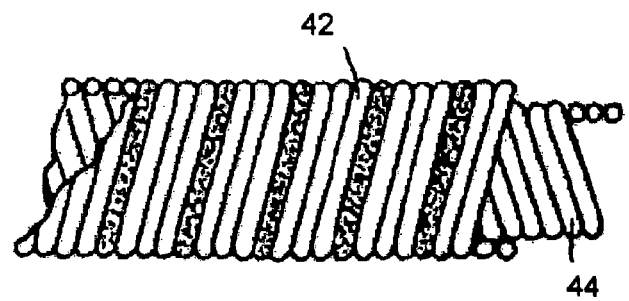
FIG. 3 illustrates an example of a multifilar cross-wound coil.

Alternatively, coil 30 may be formed of cross-wound multifilar or multifilar single coil wire. Multifilar cross-wound coils are described in U.S. Pat. No. 4,932,419 to de Toledo which is herein incorporated by reference. As represented in FIG. 3, a cross-wound multifilar coil consists essentially of a first inner coil 44 of multiple coil wires wound in a first helical direction and a second outer coil 42 of multiple coil wires disposed about the first coil and wound in a second opposite helical direction. Coil over core wires tend to wind up and store energy when torqued rather than transmitting the torque. Multifilar coils provider less wind up and therefore lessen the potential for the distal tip of the wire to whip while the proximal end is being turned.

Bonding core 20 to coil 30 also improves the torque transmission of guide wire 10. Coil 30 may be bonded to core 20 along the length of core 20 or in discrete sections. Bonding may be achieved in a variety of ways including using adhesives, brazing, welding, crimping, and swaging. Welding may be done through any of the techniques known in the art including spot welding using laser or resistance welding or ball welding using laser or plasma welding. Soldering may be done through any of the techniques known in the art and must include the step of preparing the surface of the Nitinol core 20 by plating or etching. Preferably the coil 30 will be bonded to the core 20 by laser spot welding thereby removing the need for preparing the surface of the core 20. Laser spot welding is also advantageous because it may be done through coatings.

An alternative method of bonding the coil 30 to the core 20 is to provide a stainless steel hypotube (not shown) with an inner diameter dimensioned to closely fit about core 20. The stainless steel hypotube may then be crimped onto core 20 and the coil 30 wound about the hypotube. The hypotube then provides a surface which is much easier to bound to a stainless steel coil 30 using conventional methods. Metal a foils or other materials may also be used as an intermediate which facilitates bonding between the coil 30 and the core 20.

Yet another bonding method utilizes the polymer jacket 40 of the distal tip. The polymer may be applied in a manner that allows the polymer to flow between the coil and core. The polymer will provide a high integrity bond which will help to prevent the polymer jacket from separating from the coil 30 and bond the coil to core 20. In addition to the these improvements, the polymer coating will make a better transition from the core 20 to the distal portion 25. A tip bonded in this manor provides a further improvement by producing coloration differences between the coil wire and polymer. These differences act as stripes for the detection of guidewire advance in endoscopy application.

The distal portion 25 of core wire 20 may further include a polymer tip 40. Polymer tip 40 serves several functions. Polymer tip 40 improves the flexibility of the distal portion 25 of core wire 20. Choice of polymers for polymer tip 40 will vary the flexibility of the distal portion 25 of core wire 20. For example, polymers with a low durometer or hardness will make a very flexible or floppy tip. Conversely, polymers with a high durometer will make a wire tip which is stiffer.

Polymer tip 40 also provides a more atraumatic tip for guide wire 10. An atraumatic tip is better suited for passing through fragile body passages. Finally, polymer tip 40 may act as a binder for radio-opaque materials. Loading polymers with radio-opaque materials is well known in the art for producing a bright image under fluoroscopy and thereby allowing the user of guide wire 10 a better understanding of where the distal portion 25 of guide wire 10 is located within a patient's body. Suitable medical grade radio-opaque materials include tungsten, platinum, and iridium.

Suitable polymeric materials for polymer tip 40 include urethanes, elastomeric nylons such as Pebax, silicones, and co-polymers. Polymer tip 40 may be a single polymer, multiple layers, or a blend of polymers.

Coating (not shown) may also be done to the wire proximal to polymer tip 40. Hydrophobic coatings such as fluoropolymers provide a dry lubricity which improves guide wire handling and device exchanges. A second lubricious polymer (not shown) may coat distal portion 25 of guide wire 10 or the entire wire 10. Lubricious coatings improve steerability and improve lesion crossing capability. Suitable lubricious polymers are well known in the art and may include hydrophilic polymers.

Guide wire 10 may further include a colored coating. Colored guide wires are described in detail in U.S. Pat. No. 5,739,779 to Rowland which is herein incorporated by reference. In general, colored coatings may improve the visibility of the guide wire when it is being used in an endoscopic procedure. Striping may also be done. Striping allows the physician to gauge wire movement and position. Striping may be achieved by spray coating different colors on the wire 10. Another way to stripe the wire 10 is to coat the wires of coil 30 prior to winding.

FIG. 2 depicts a second embodiment of the high performance coil wire where like elements are similarly numbered. All design advantages, materials of construction, and methods of manufacture are similar to those described above unless explicitly modified below. Guide wire 10 is comprised of a solid core 20 surrounded by a coil 30. The distal portion 25 of core 20 may be tapered as described above or preferably is not tapered. Similar to the embodiment of FIG. 1, the distal portion 35 of coil 30 changes pitch to provide a softer less traumatic tip.

Guide wire 10 further includes a rounded tip 37. Tip 37 may be polymeric or a metal tip welded to the distal portion 35 of coil 30. Unlike common spring tipped guide wires, guide wire 10 does not have a safety ribbon connecting core 20 to tip 37. Instead guide wire 10 may include a polymer 40 which may be flowed into the space between coils 35 and the space between the distal portion 25 and tip 37. Suitable polymers are described above where choice of polymer may control the flexibility of the tip. Polymer 40 may also be loaded with radio-opaque materials. Finally, guide wire 10 may be coated as described above and may also include various colors or stripes. The distal portion of guide wire 10 is thereby provided with a very floppy tip which uses polymer 40 as a safety ribbon instead of a metallic safety ribbon. Guide wire 10 is provided with the advantage that core 20 does not need to be ground.

While the specification describes the preferred designs, materials, methods of manufacture and methods of use, those skilled in the art will appreciate the scope and spirit of the invention with reference to the following claims.

We claim:

1. A guide wire comprising:
an elongate core defining a proximal end and a distal end;
a continuous, unitary coil exhibiting an outer diameter and an inner diameter surrounding a portion of the core, with a portion of the coil extending beyond the distal end of the core by a plurality of turns of the coil, the inner diameter of the coil defining an internal area inside the coil along the portion of the coil that extends beyond the core; and
a polymer contacting the distal end of the core and entirely filling the internal area, without extending beyond a distal end of the coil; and
a metal tip extending from a distal end of the polymer and contacting a distal surface of the coil.

2. A guide wire comprising:
an elongate core composed of a nickel-titanium alloy including a proximal end and a distal end;
a continuous, unitary coil exhibiting an outer diameter and an inner diameter surrounding a portion of the core, the inner diameter of the coil defining an internal area inside the coil;
a first polymer contacting the core and at least partially filling the internal area, without extending beyond a distal end of the coil; and
a second polymer defining a tip and extending from a distal end of the first polymer and contacting a distal surface of the coil.

3. The guide wire of claim 2, wherein a portion of the coil extends beyond the distal end of the core by a plurality of turns of the coil.

4. The guide wire of claim 3, wherein the first polymer entirely fills the internal area along the portion of the coil that extends beyond the core.

5. The guide wire of claim 2, wherein the core is not tapered along its distal portion.

6. A guide wire comprising:
an elongate core composed of a nickel-titanium alloy including a proximal end and a distal end;
a continuous, unitary coil exhibiting an outer diameter and an inner diameter, composed of a second material, surrounding a portion of the core, the inner diameter of the coil defining an internal area inside the coil;
a polymer contacting the core and at least partially filling the internal area, without extending beyond a distal end of the coil;
a tip extending from a distal end of the polymer and contacting a distal surface of the coil; and
wherein the core is not tapered along its distal portion.

7. The guide wire of claim 6, wherein a portion of the coil extends beyond the distal end of the core by a plurality of turns of the coil.

8. The guide wire of claim 7, wherein the polymer entirely fills the internal area along the portion of the coil that extends beyond the core.

9. The guide wire of claim 7, wherein the portion of the coil extending beyond the distal end of the core has a pitch different from a remaining portion of the coil.

10. A guide wire comprising:
an elongate core defining a proximal end and a distal end;
a continuous, unitary coil having a circular cross-section, exhibiting an outer diameter and an inner diameter surrounding a portion of the core, with a portion of the coil extending beyond the distal end of the core by a plurality of turns of the coil, the inner diameter of the coil defining an internal area inside the coil along the portion of the coil that extends beyond the core;
a polymer contacting the distal end of the core and entirely filling the internal area, without extending beyond a distal end of the coil; and
a metal tip extending from a distal end of the polymer and contacting a distal surface of the coil.

11. A guide wire comprising:
an elongate core composed of a nickel-titanium alloy including a length, a proximal portion, a distal end, and a constant diameter along the length;
a continuous, unitary coil exhibiting an outer diameter and an inner diameter composed of a second material and that surrounds and extends along the length of the core, the inner diameter of the coil defining an internal area inside the coil;
a first polymer contacting the core and at least partially filling the internal area, without extending beyond a distal end of the coil; and
a second polymer defining a tip and extending from a distal end of the first polymer and contacting a distal surface of the coil.

12. The guide wire of claim 11, wherein the coil surrounds the entire length of the core.

13. The guide wire of claim 11, wherein the coil comprises a pitch that varies at least once along the length of the core.

14. The guide wire of claim 11, wherein the coil comprises a coating.

15. The guide wire of claim 14, wherein the coating is lubricious.

16. The guide wire of claim 14, wherein the coating is colored.

17. The guide wire of claim 11, wherein the coil comprises a rectangular cross-section.

18. The guide wire of claim 11, wherein the coil comprises a circular cross-section.

19. The guide wire of claim 11, wherein the coil comprises a multifilar wire.

20. The guide wire of claim 11, wherein the polymeric tip is in contact with a distal portion of the coil.

21. The guide wire of claim 11, wherein a portion of the coil extends beyond the distal end of the core by a plurality of turns of the coil.

22. The guide wire of claim 21, wherein the first polymer entirely fills the internal area along the portion of the coil that extends beyond the core.

23. The guide wire of claim 11, wherein the core is not tapered along its distal portion.

24. A guide wire comprising:
an elongate core composed of a nickel-titanium alloy including a length, a proximal portion, a distal end and a constant diameter along the length;
a continuous, unitary coil exhibiting an outer diameter and an inner diameter composed of a second material comprising stainless steel and that surrounds a portion of the core, the inner diameter of the coil defining an internal area inside the coil;
a polymer contacting the core and at least partially filling the internal area, without extending beyond a distal end of the coil;
a tip extending from a distal end of the polymer and contacting a distal surface of the coil; and
wherein the core is not tapered along its distal portion.

25. The guide wire of claim 24, wherein a portion of the coil extends beyond the distal end of the core by a plurality of turns of the coil.

26. The guide wire of claim 25, wherein the polymer entirely fills the internal area along the portion of the coil that extends beyond the core.

27. The guide wire of claim 25, wherein the portion of the coil extending beyond the distal end of the core has a pitch different from a remaining portion of the coil.

28. A guide wire comprising:
an elongate core composed of a nickel-titanium alloy including a length, a proximal portion, a distal end, and a constant diameter along the length;
a continuous, unitary coil composed of a second material and that surrounds a portion of the core, with a portion of the coil extending beyond the distal end of the core by a plurality of turns of the coil, the inner diameter of the coil defining an internal area inside the coil along the portion of the coil that extends beyond the core; and
a polymer contacting the distal end of the core and entirely filling the internal area, without extending beyond a distal end of the coil; and
a metal tip extending from a distal end of the polymer and contacting a distal surface of the coil.

29. A guide wire comprising:
an elongate core composed of a nickel-titanium alloy including a proximal end and a distal end;
a continuous, unitary coil exhibiting an outer diameter and an inner diameter composed of a second material and that surrounds a portion of the core, wherein the coil comprises a first coil portion having a first pitch and a second coil portion having a second pitch greater than the first pitch;
the inner diameter of the coil defining an internal area inside the coil;
a first polymer contacting the core and at least partially filling the internal area, without extending beyond a distal end of the coil; and
a second polymer defining a tip and extending from a distal end of the first polymer and contacting a distal surface of the coil.

30. The guide wire of claim 29, wherein the second coil portion surrounds the distal end of the core.

31. The guide wire of claim 29, wherein the coil surrounds the entire length of the core.

32. The guide wire of claim 29, wherein the coil extends along the core from the portion of the core near the proximal end of the core to a portion of the core near a distal end of the core.

33. The guide wire of claim 29, wherein the second material comprises stainless steel.

34. The guide wire of claim 29, wherein the second material comprises a precipitation hardenable alloy.

35. The guide wire of claim 29, wherein a distal portion of the core is tapered.

36. The guide wire of claim 29, wherein the tip includes a radio-opaque material.

37. The guide wire of claim 29, wherein the coil comprises a coating.

38. The guide wire of claim 37, wherein the coating is lubricious.

39. The guide wire of claim 37, wherein the coating is colored.

40. The guide wire of claim 29, wherein the coil comprises a rectangular cross-section.

41. The guide wire of claim 29, wherein the coil comprises a circular cross-section.

42. The guide wire of claim 29, wherein the coil comprises a multifilar wire.

43. The guide wire of claim 29, wherein a portion of the coil extends beyond the distal end of the core by a plurality of turns of the coil.

44. The guide wire of claim 43, wherein the first polymer entirely fills the internal area along the portion of the coil that extends beyond the core.

45. The guide wire of claim 29, wherein the core is not tapered along its distal portion.

46. A guide wire comprising:

an elongate core composed of a nickel-titanium alloy including a proximal end and a distal end;

a continuous coil exhibiting an outer diameter and an inner diameter composed of a second material and that surrounds a portion of the core, the inner diameter of the coil defining an internal area inside the coil;

a polymer contacting the core and at least partially filling the internal area, without extending beyond a distal end of the coil;

a tip extending from a distal end of the polymer and contacting a distal surface of the coil; and wherein the core is not tapered along its distal portion.

47. The guide wire of claim 46, wherein the coil surrounds the entire length of the core.

48. The guide wire of claim 46, wherein the tip includes a radio-opaque material.

49. The guide wire of claim 46, wherein the coil comprises a coating.

50. The guide wire of claim 46, wherein the coil comprises a rectangular cross-section.

51. The guide wire of claim 46, wherein the coil comprises a multifilar wire.

52. The guide wire of claim 46, wherein a portion of the coil extends beyond the distal end of the core by a plurality of turns of the coil.

53. The guide wire of claim 52, wherein the polymer entirely fills the internal area along the portion of the coil that extends beyond the core.

54. The guide wire of claim 52, wherein the portion of the coil extending beyond the distal end of the core has a pitch different from a remaining portion of the coil.

* * * * *